United States Patent [19]

Raymond et al.

[11] Patent Number: 5,284,153
[45] Date of Patent: Feb. 8, 1994

[54] METHOD FOR LOCATING A NERVE AND FOR PROTECTING NERVES FROM INJURY DURING SURGERY

[75] Inventors: Stephen A. Raymond, Charlestown; Gary R. Strichartz, West Roxbury; James H. Philip, Chestnut Hill; Daniel B. Raemer, Brookline, all of Mass.; Martyn A. Vickers, Jr., Augusta, Me.

[73] Assignee: Brigham and Women's Hospital, Boston, Mass.

[21] Appl. No.: 868,387

[22] Filed: Apr. 14, 1992

[51] Int. Cl.⁵ .............................................. A61B 5/05
[52] U.S. Cl. .................................. 128/741; 128/774; 607/143
[58] Field of Search ............... 128/741, 739, 740, 742, 128/744, 745, 746, 733, 774, 782, 783, 421, 419 R; 607/143; 364/413.01, 413.02

[56] References Cited

U.S. PATENT DOCUMENTS

| | | | |
|---|---|---|---|
| 2,704,064 | 3/1955 | Fizzell et al. | 128/741 |
| 3,364,929 | 1/1968 | Ide et al. | 128/741 |
| 3,641,993 | 2/1972 | Gaarder et al. | 128/733 |
| 3,664,329 | 5/1972 | Naylor | 128/741 |
| 3,672,162 | 8/1972 | Colyer | 128/642 |
| 3,830,226 | 8/1974 | Staub et al. | 128/908 |
| 4,099,519 | 7/1978 | Warren | 128/741 |
| 4,103,678 | 8/1978 | Karacan et al. | 128/774 |
| 4,207,897 | 6/1980 | Lloyd et al. | 606/23 |
| 4,291,705 | 9/1981 | Severinghaus et al. | 128/733 |
| 4,515,166 | 5/1985 | Timm | 128/694 |
| 4,515,168 | 5/1985 | Chester et al. | 128/741 |
| 4,542,753 | 9/1985 | Brenman et al. | 128/788 |
| 4,585,005 | 4/1986 | Lue et al. | 128/419 R |
| 4,777,952 | 10/1988 | Pavel | 128/419 S |
| 4,811,742 | 3/1989 | Hassel et al. | 128/733 |
| 4,815,475 | 3/1989 | Burger | 128/741 |
| 4,817,628 | 4/1989 | Zealear et al. | 128/741 |
| 4,848,361 | 7/1989 | Penney et al. | 128/774 |
| 4,892,105 | 1/1990 | Prass | 128/741 |
| 4,909,263 | 3/1990 | Norris | 128/788 |
| 4,913,162 | 4/1990 | Leang et al. | 128/774 |
| 4,926,865 | 5/1990 | Oman | 128/421 |
| 4,928,706 | 5/1990 | Trick | 128/774 |
| 4,949,721 | 8/1990 | Toriu et al. | 128/421 |
| 4,962,766 | 10/1990 | Herzon | 128/741 |
| 4,977,895 | 12/1990 | Tannenbaum | 128/421 |
| 5,007,902 | 4/1991 | Witt | 604/117 |
| 5,020,542 | 6/1991 | Rossmann et al. | 128/741 |
| 5,092,344 | 3/1992 | Lee | 128/741 |
| 5,125,406 | 6/1992 | Goldstone et al. | 128/642 |
| 5,131,401 | 7/1992 | Westenskow et al. | 128/741 |

OTHER PUBLICATIONS

Ford et al. *Regional Anesth* 9:73-77 (1984) "Electrical Characteristics . . . Localization".
Greenblatt et al. *Anesth Analg* 41:599-602 (1962) "Needle Nerve Stimulator-Locator".
Raj, P. *Clinical Issues in Regional Anesth I*: 1-6 (1985) "The Use of Peripheral Nerve . . . Anesthesia".
Pither et al. *Regional Anesth* 10:49-58 (1985) "The Use of Peripheral . . . Clinical Applications".
Raj et al. *Regional Anesth* 5:14-21 (1980) "Use of the Nerve Stimulator for Peripheral Blocks".
Raj et al. *Anesth Analg* 52:897-903 (1973) "Infraclavicular Brachial Plexus Block-A New Approach".

*Primary Examiner*—Stephen C. Pellegrino
*Assistant Examiner*—Guy V. Tucker
*Attorney, Agent, or Firm*—Sterne, Kessler, Goldstein & Fox

[57] ABSTRACT

The present invention is directed to a method and apparatus for locating and identifying the function of specific peripheral nerves. In one embodiment, the present invention takes the form of a nerve stimulator which is used to locate nerves to assist in the administration of regional anesthesia. In another embodiment, the nerve stimulator is used to locate, identify the function of, and guard against the inadvertent cutting of specific nerves during surgical procedures. The apparatus of the present invention includes a stimulus delivery means, a response-detecting means and a means for automatically modulating the magnitude of the stimulus.

19 Claims, 10 Drawing Sheets

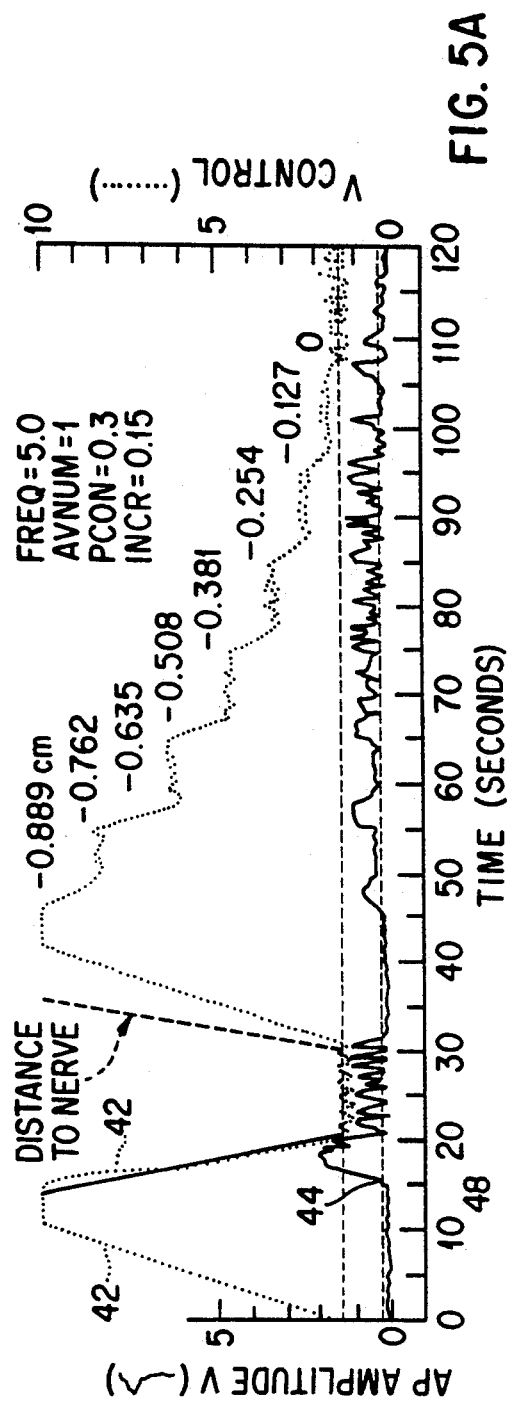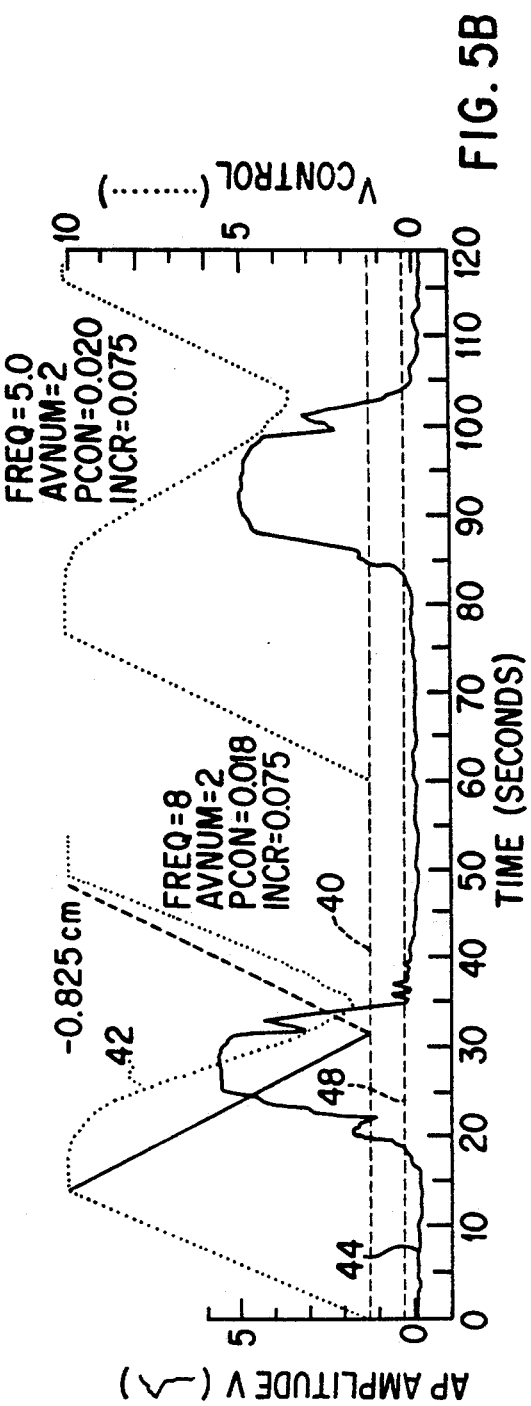

METHOD FOR LOCATING A NERVE AND FOR PROTECTING NERVES FROM INJURY DURING SURGERY

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

FIELD OF THE INVENTION

The present invention relates to a method and apparatus for locating a nerve, and more particularly the invention relates to a method and apparatus for precisely locating and identifying a specific peripheral nerve; and a method and apparatus for testing tissue during surgery to determine if it contains or is near an important nerve.

BACKGROUND OF THE INVENTION

The practice of regional anesthesia (the administration of anesthesia to a specific body region) is not new. Today, increasing numbers of patients are receiving nerve blocks for anesthetic purposes during surgery and for extended relief of trauma or chronic pain.

Successful administration of regional anesthesia depends primarily on the accurate placement of anesthesia in relation to the target nerve. For sensory nerves, accuracy of placement is determined by paresthesia (a buzzing or tingling sensation) reported by the patient to the physician. Obviously, the success rate of a nerve block will be low when the patient gives an inaccurate report of paresthesia or when the patient is disoriented, sedated or otherwise not fully functional. Equally critical to the success of a nerve block is the skill or experience of the anesthesiologist attempting to localize a nerve.

In an effort to increase the success rate of a nerve block, some anesthesiologists x-ray patients before administering anesthetic solution to determine the exact location of the anesthesia needle vis-a-vis the target nerve. Although somewhat helpful, this technique proves to be impractical, expensive, and not always readily available.

More recently, peripheral nerve stimulators have been put into practice as a means of effectively locating peripheral nerves. Nerve localization via electrical stimulation is based on the fact that an electrical pulse can stimulate a nerve fiber to contract an innervated muscle or cause paresthesia in the case of sensory nerve stimulation.

Over the years, nerve stimulators have taken the form of insulated (or uninsulated) anesthesia needles connected to a source of electricity. To localize a nerve, the electrified anesthesia needle is placed within the tissue of the body in the vicinity of the nerve to be blocked. The needle is then used as a stimulating probe until stimulation of the target nerve is achieved as determined by visually detecting muscle contractions or by eliciting a report that the patient feels the stimulus. The current supplied by the electrical source is reduced while the anesthetist simultaneously advances or redirects the needle within the tissue until nerve stimulation is obtained using a lower amperage current. An injection of a portion of the anesthetic dose is then administered to the patient to terminate the response of the nerve to the electrical pulse. If the nerve response is terminated, the anesthesia needle is deemed to be in the vicinity of the target nerve (often with actual needle-to-nerve contact), and the remaining dose of anesthetic is administered to the patient. This same technique is employed regardless of whether the nerve to be localized is motor or sensory. A description of this nerve localization technique is discussed in greater detail in Raj et al., "Use of the Nerve Stimulator for Peripheral Blocks", Regional Anesthesia, April-June 1980, pp. 14-21.

Examples of nerve stimulators for assisting in the administration of anesthesia may be found in U.S. Pat. No. 3,682,162 to Coyler and U.S. Pat. No. 4,515,168 to Chester et al. The Coyler patent generally discloses a combined electrode and syringe needle which acts as a stimulation probe when the syringe needle is connected to an electrical supply.

The Chester et al. patent discloses a nerve stimulator which is clamped onto the syringe of a conventional syringe and anesthesia needle assembly. The unit contains a power supply, a pulse generating circuit, and a manually controlled current-adjusting potentiometer which allows the operator to adjust the current supplied to the needle.

Although both of the above-described devices are effective in stimulating a peripheral nerve, errors in administering anesthesia to obtain a nerve block may be encountered. This occurs because the success of the nerve block is dependent upon the cooperation of the patient and the skill of the anesthesiologist. For example, when stimulating sensory nerves, the anesthesiologist must rely on the patient's ability to perceive and to describe the degree of tingling for information regarding the effectiveness of electrical nerve stimulation. Thus, if the patient is unable to communicate or accurately evaluate paresthesia, anesthesia may be delivered to an improper location resulting in an ineffective nerve block or an overdose of anesthesia. On the other hand, when stimulating a motor nerve, the anesthesiologist must pay close attention to the associated muscle to avoid missing any contraction of the muscle or other anatomical cue indicative of needle location relative to the target nerve. Furthermore, regardless of whether the nerve to be localized is motor or sensory, the anesthesiologist must manually adjust the strength of the electrical current. This manual adjustment requires an assistant who is not "scrubbed" (i.e. whose hands do not need to remain sterile and who can therefore handle the control knob, which is not sterilized) thereby leaving room for human error which could, in extreme cases, cause infection by contamination and/or permanently damage the peripheral nerve. Thus, within the field of regional anesthesia, a need exists for a nerve stimulator which overcomes the weaknesses of the aforementioned devices and effectively localizes peripheral nerves for anesthetic purposes.

Nerves are localized for other, non-anesthetic purposes and an electrical nerve stimulator (although used in a different manner) can be useful for these purposes as well. For example, during surgical procedures, the operating surgeon must avoid cutting nerves which are essential for specific motor or sensory functions. To avoid cutting such nerves, the surgeon may use a nerve stimulator to determine the exact location of a nerve to guard against inadvertent cutting.

An example of a nerve stimulator used for this purpose is disclosed in U.S. Pat. No. 2,704,064 to Fizzell et al. The Fizzell et al. patent discloses a neuromuscular stimulator having two probes for passing a current to a subcutaneous nerve. The probes are placed on the body in the area of the nerve to be stimulated and an operating surgeon watches for a response to the applied current. If a response to the current is observed, the surgeon avoids cutting in that particular area to prevent inadvertent severing of a nerve. Thus, by probing carefully, the surgeon may excise tumorous tissue, for example, without destroying nerves essential for specific body functions.

The Fizzell et al. device suffers from some of the same disadvantages as the nerve stimulators used for regional anesthesia, including manual adjustment of electrical current and close observation of associated muscles by the operating surgeon or an assistant and inability to localize autonomic nerves or visceral somatic nerves. Thus, within the field of surgery there also exists a need for a nerve stimulator which localizes and guards peripheral nerves easily and effectively.

SUMMARY OF THE INVENTION

It was with these needs in mind that the present invention was developed. In one aspect of the present invention, a nerve stimulator is used to locate nerves to assist in the administration of regional anesthesia. The nerve stimulator or locator includes an anesthesia (stimulating) needle, which is coupled to an electrical source, and a device for detecting responses of the nerve to electrical stimuli. The amount of current generated by the electrical source is automatically controlled so as to maintain the signal generated as a function of the response of the nerve to the stimuli. The closer the stimulating needle comes to the nerve, the higher the responses detected will be, which in turn will automatically decrease the electrical stimulus.

The nerve locator is used by inserting the anesthesia needle into the tissue of the body in the vicinity of the nerve to be located. An electrical current is then sent to the tip of the needle and if there is a response by the nerve (i.e. if an action potential is elicited), the response detecting device measures the response. Based on the nervous response, the next current pulse sent to the needle decreases or increases as the needle is advanced or directed within the body tissue. If the response detecting device does not detect a response (or action potential) of a predetermined value, a higher amperage current is sent to the anesthesia needle. As the response detecting device begins to detect a response to the stimuli, and as the needle is inserted deeper within the tissue in the direction of the nerve to be located, the current intensity is automatically decreased as the needle approaches the nerve. When a stimulating current of a predetermined minimum value is reached, the nerve has been "found" or located. At this time, a test dose of anesthetic is administered to the patient to verify accuracy of anesthetic placement vis-a-vis the target nerve. The distance of the anesthesia needle in relation to the target nerve, which is related to the stimulus intensity needed to evoke a response, may thus be indicated visually or audibly throughout the locating procedure.

In another aspect of the present invention, a nerve stimulator is used to locate, identify the function of, and guard against the inadvertent cutting of specific peripheral nerves during surgical procedures. The nerve locator or guard includes a surgical probe which is coupled to an electrical source and a device for detecting responses of the nerve to electrical stimuli. The amount of current generated by the electrical source is automatically controlled to maintain the signal measured as a function of the response of the nerve to various stimuli.

The nerve guard is used by elevating tissue to be sectioned on the stimulating probe. An electrical current is then sent to the probe and if there is a response by a nerve within the elevated tissue (i.e. if an action potential is elicited, if the associated muscle responds, or if an organ innervated by the nerve changes its size or functional activity), the response detecting device measures the response. Based on the nervous response, the next current pulse sent to the probe decreases or increases as the elevated tissue is supported thereon. If the response detecting device does not detect a response or action potential of a predetermined value, a higher amperage current is sent to the stimulating probe. As the response detecting device begins to detect a response to the stimuli, the intensity of the current is decreased. The automated stimulus control thus converges on a stimulus intensity that is just sufficient to insure, the continued responses by the nerve, and the intensity thus tracked is a useful indication of whether the tissue contains or is near to a nerve that is responsible for a specific motor function. Thus, if this motor function is to be preserved, the nerve guard of the present invention identifies whether the tissue on the probe contains nerves which are responsible for the particular motor function. In one aspect of the invention, the responses of the nerve to the stimuli may be indicated visually or audibly throughout the procedure.

Thus, both the nerve locating and nerve guarding aspects of the present invention seek to overcome each of the above-described disadvantages of nerve stimulators heretofore known.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 5 is a series of graphs showing the tracking and stability of the nerve locating embodiment together with the amplitude of nerve responses in the nerve being localized;

DETAILED DESCRIPTION OF THE DRAWINGS

Figure 1:
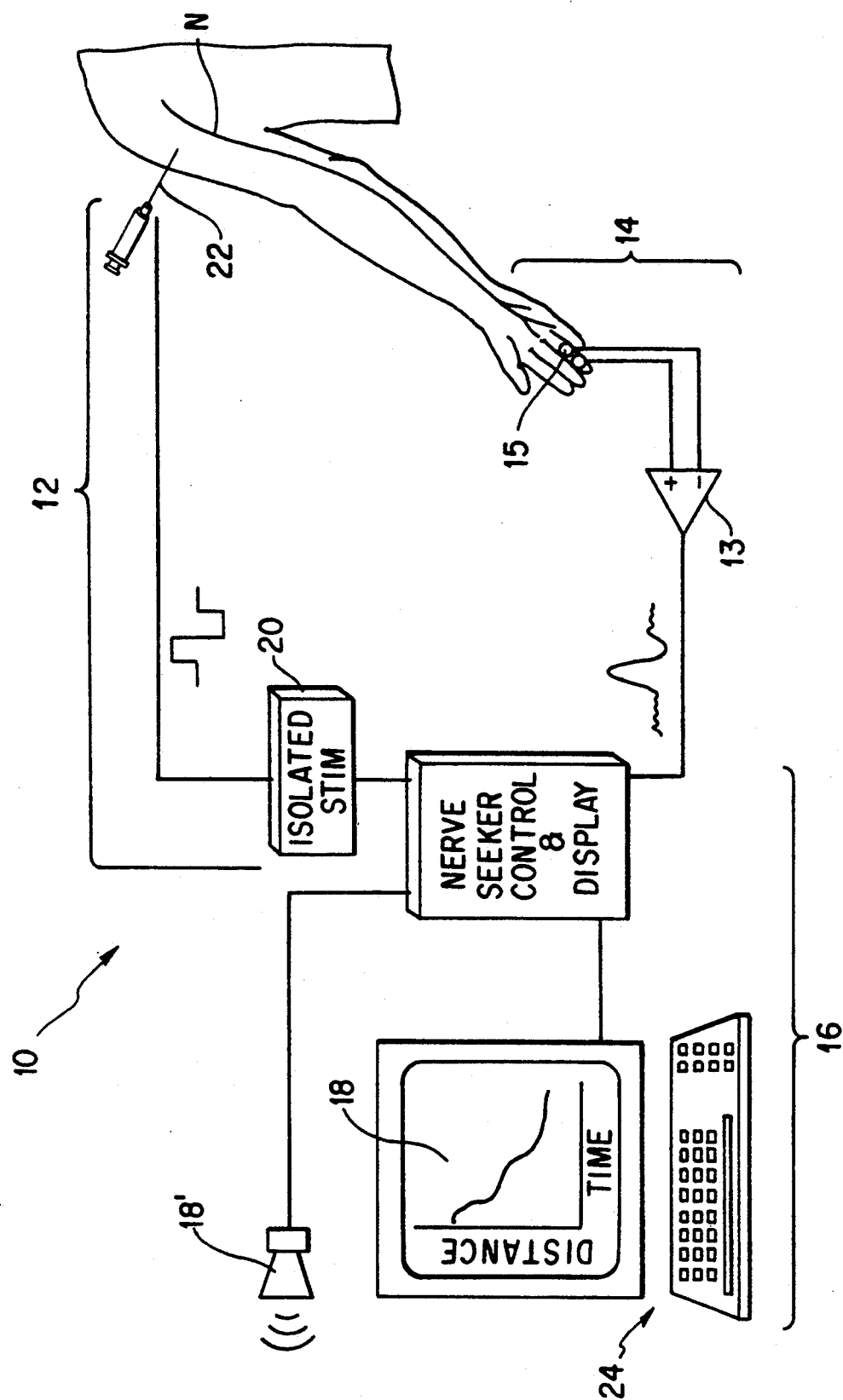
FIG. 1 is a schematic drawing of the component parts of the embodiment for locating nerves for delivery of drugs, such as anesthetics.

With continuing reference to the drawing figures in which similar reference numerals are used throughout the description of the invention to describe similar features of the invention, the nerve locator of the present invention for locating a peripheral nerve is shown generally at 10 in FIG. 1. Nerve locator 10 generally includes a stimulus generating and delivery means 12, a response-detecting means 14, and a stimulus control or modulating means 16.

Stimulus generating and delivery means 12 includes a stimulator circuit 20 and a stimulating probe 22. Stimulator circuit 20 generates a symmetric biphasic square pulse current in response to a timed trigger from stimulus control means 16. The circuit initially generates an analog triangular voltage waveform whose slope and duration can be varied. This waveform is applied to a differentiator circuit to yield a biphasic square voltage pulse. A voltage-controlled current generator using power MOSfets (available from International Rectifier, El Segundo, Calif.) and high voltage batteries converts this biphasic voltage signal to a pulse current which is deliverable to the target nerve through a probe 22. The voltage-controlled current generator controls the magnitude (i.e. the duration and strength) of the pulse delivered to the nerve in response to triggers from stimulus control means 16. For effective nerve stimulation, input and output specifications of stimulator circuit 20 have been determined as follows:

| Control Signals | |
| --- | --- |
| Volatage control | 0-10 V DC, from Digital to Analog Converter of 16 |
| Voltage Pulse Controlling Duration of Current Pulse from 16 | |
| Amplitude | 13.5 V |
| Duration | 56-570 μs |
| Biphasic Voltage Pulse Converted to a biphasic current pulse from 16 | |
| Amplitude | 0-10.6 V |
| Half Wave Duration | 56-570 μs |
| Output, Biphasic Current Pulse from 20 | |
| Amplitude | 0-20 mA (delivered to a <5 KΩ load, requiring less than 100 V) |
| Half Wave Duration | 56-570 μs |
| Output Impedance | 15 MΩ |
| Rise Time (2K load) | 13 μs |
| Switch Time (transition of biphasic pulse) | 20 μs |
| Fall Time | 30 μs |

The biphasic current pulses generated by stimulator circuit 20 are delivered to the nerve through stimulating probe 22. Stimulating probe 22 preferably takes the form of an insulated needle. Use of an insulated needle insures that the source of the current coincides with the tip of the needle. An example of a suitable needle is the Bardic stainless steel, beveled-tip needle having an "around needle catheter" available from Regional Masters Corporation, International Medical Technology Corporation and HDC Corporation. The needle should preferably be 22-23 gauge and 1½ to 3 inches in length. Although an insulated, rounded or beveled-tip needle is preferred, an uninsulated or pinpoint needle may also be used as a stimulating probe.

The response of the nerve to the pulse delivered by stimulating probe 22 is detected and recorded by a response-detecting means 14. Response-detecting means 14 is capable of detecting and recording potentials produced within the nerve itself (nerve action potentials) or those produced within the fibers of associated skeletal muscle (muscle action potentials) which occur as a result of stimulation of the target nerve. Response-detecting means 14 may take the form of electrodes 15 similar to those used with an electromyograph (EMG) or gauges to detect changes in size, shape or function of an innervated organ. Response-detecting means 14 further includes a variable high-gain amplifier module 13 which is capable of boosting signals from surface electrodes (or from insertion electrodes) to levels appropriate for analog-digital (A/D) conversion (approximately 1-5 V). A modular differential electrometer with continuously variable gain, such as one available from MetaMetrics Corporation, Cambridge, Mass., is preferably used to prevent polarization of electrodes 15.

The response detecting means may also include the user or other observer, who will detect the response and by depressing a switch indicate to the control means 16 that the stimulus is effective. Thus it is possible to take advantage of the automatic adjustment of the stimulus by manually detecting the response, and this feature is incorporated as an alternate response-detecting means as well as an override of other transducers and amplifiers serving as response detecting means.

The amplified response of the nerve is transmitted to a stimulus modulating or control means 16 which modulates the magnitude of the next pulse or stimulus as a function of the response received from response-detecting means 14. The magnitude of the stimulus is controlled by a signal referred to as $V_{control}$ (control voltage) produced by modulating means 16. The voltage of the pulse sent to stimulator circuit 20 is determined by a software program which will be discussed in greater detail below. If the response detected by response-detecting means 14 is strong, stimulus modulating means 16 strongly reduces $V_{control}$ signal on the digital to analog convertor, which in turn reduces the magnitude of the next pulse generated by stimulator circuit 20. If, however, the nerve response is weak (for example, if the needle is not close to the target nerve or if the needle has gone past the nerve), stimulus modulating means 16 produces a $V_{control}$ signal which increases the magnitude of the next pulse generated by the circuit.

Stimulus modulating means 16 includes a computer 24 which utilizes data acquisition hardware and software. For test purposes, an Intel 80286-based personal computer and a Metabyte 16 data acquisition board (available from Metabyte Corporation, Taunton, Mass.) was used. The data acquisition board should have at least a one channel (12 bit) analog-digital converter, two separate digital-analog converters, and timer chips. The data acquisition software is written to determine the value of $V_{control}$ based on the settings of two groups of parameters discussed in greater detail below.

For purposes of safety and reduction of stimulus artifacts, the stimulus pulse was isolated from ground by installing an isolation amplifier between the digital to analog converter providing $V_{control}$ and the simulator circuit. A phototransistor was used to isolate the digital trigger.

In a preferred embodiment, stimulus modulating means 16 may also include a needle to nerve distance indicator program which plots (on the monitor of computer 24) the value of each action potential detected by response-detecting means 14 and the strength of each pulse delivered to the nerve as the target nerve is approached. A plotting of these values is shown at 18 in FIG. 1. If desired, the needle to nerve distance indicator program may be made audible (18') by using a counter chip and speaker within computer 24 to produce a tone which is indicative of the location of the needle vis-a-vis the target nerve. For example, the pitch of the tone may rise as the magnitude of the stimulus is reduced by stimulator circuit 20. Thus, an increasingly high-pitched tone would indicate that the stimulating probe (needle) is approaching the target nerve. Alternatively, a voice-synthesizing module may be used to "speak" the converted parameter of the distance of the needle to the nerve in intelligible English language, changing words (e.g. 10 cm, 9 cm, etc) as the needle approaches the nerve.

EXPERIMENTAL TESTS

To evaluate the performance of the system qualitatively and to help direct the evolution of the software for simple non-invasive recording techniques, numerous experiments were performed.

In vivo experiments were performed on three anesthetized frogs and three rats. The frogs and rats were grounded electrically by placing them on a chlorided silver plate resting on a nonconductive foam surface. Silver wires were wrapped around the toes and ankles to serve as recording electrodes. A hand-held insulated needle, which served as stimulating probe 22 was advanced through the skin of the upper thigh to localize the sciatic nerve.

Figure 2:
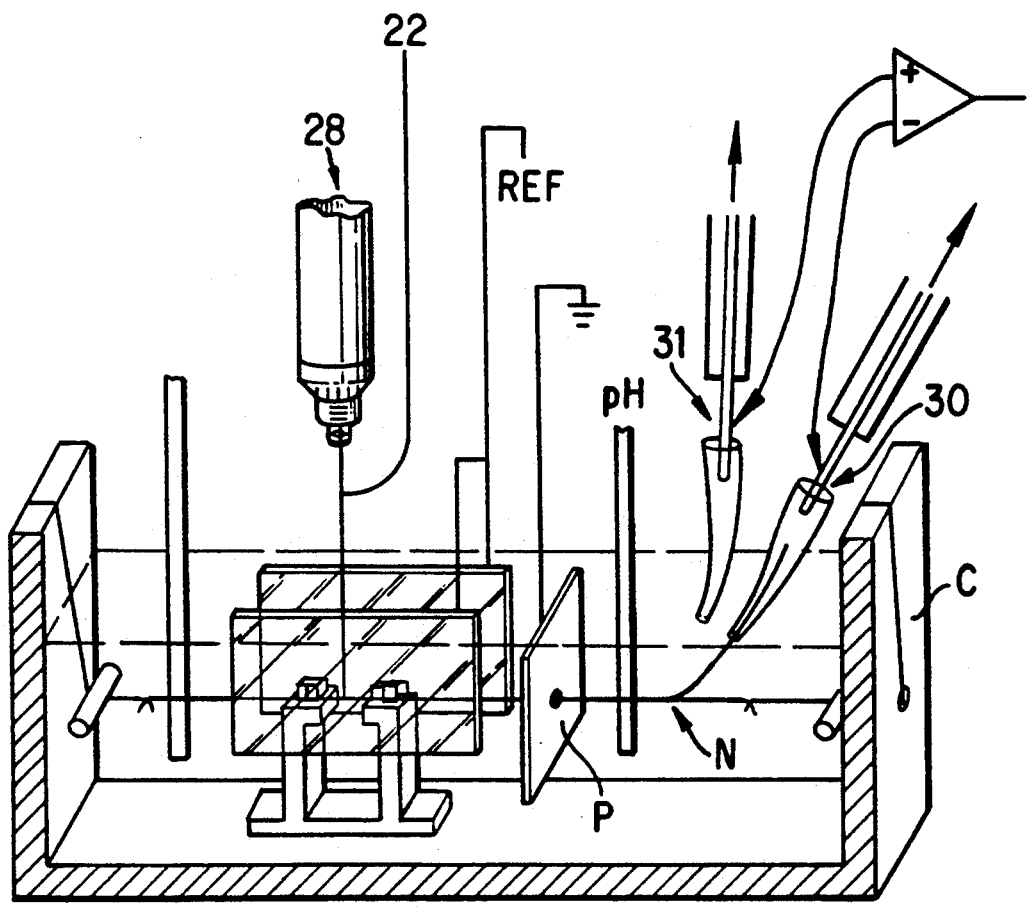
FIG. 2 is a schematic drawing of the chamber for in vitro experiments.

In vitro experiments were conducted with an isolated frog sciatic nerve in modified Boyle Conway solution. With reference to FIG. 2, the sciatic nerve N was excised between the spinal column and the ankle, and stretched within a large transparent plexiglass chamber C filled with Boyle Conway solution. Nerve N was stretched through a chlorided silver square plate P to electrically shield the recording area from the stimulated region. The tension on nerve N was sufficient to keep the nerve straight and centered, yet loose enough to allow displacement so that no nerve damage occurred if the stimulating needle (probe) 22 touched it.

The movement of the needle was measured by a micrometer 28 having a range of one inch. The micrometer settings during each approach were used to correlate the degree of needle movement with the $V_{control}$ governing the magnitude of the stimulating pulse and serving as the "distance parameter" (being in its low range, near 0 V, when the needle was near the nerve and in its high range, near 10 V, when the needle was far away from the nerve). Action potentials produced by the stimulated nerve were detected and recorded by a suction electrode 30 sized to hold one of the distal branches of the frog sciatic nerve. The nerve was referenced to a second suction electrode 31 also containing Boyle Conway solution, but without a nerve branch sucked into the electrode.

Results were obtained from trials using 24 dissected frog sciatic nerves to establish appropriate settings for the various parameters and to evaluate the capability of the system to track movement of the needle. The user-selectable parameters and their impact on the performance of the nerve locator 10 will now be discussed.

As referred to briefly above in the description of stimulus modulating means 16, two main groups of user-selectable parameters are used to "tune" the stimulus modulating means. The first set of parameters set criterion analog levels for detecting a response to the nerve. The second set of parameters controls the rate at which the device tracks the position of the stimulating needle with respect to the nerve.

CRITERION ANALOG LEVELS

There are three independent criterion level parameters: the action potential criterion level (AP-LEV), the destination voltage criterion level (D-LEV), and the maximum voltage criterion level (VMAX). The AP-LEV is the criterion level that the peak of the recorded action potential must reach in order for the stimuli delivered to the nerve to be considered successful at stimulating the target nerve. For in vitro experiments, the AP-LEV was set empirically at about 5-8% of the maximum amplitude of the fastest conducting elevation of the action potential. This range represented the lowest value yielding unambiguous activation of enough low-threshold nerve fibers to indicate effective nerve stimulation. Since the system will converge to a state where it is stimulating nerves to produce action potentials with this peak amplitude value (AP-LEV), the sensations or movements evoked by the stimulating needle during insertion will be minimized if the AP-LEV is set low.

Figure 3A:
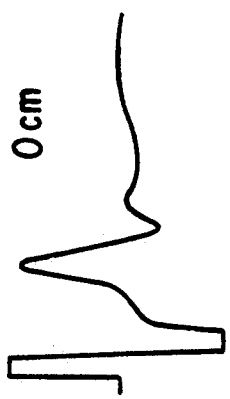
FIG. 3 is a graph of action potential peak values plotted against stimulus magnitude at several fixed distances from the nerve.
Figure 3B:
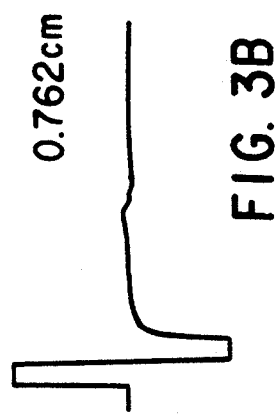
Figure 3:
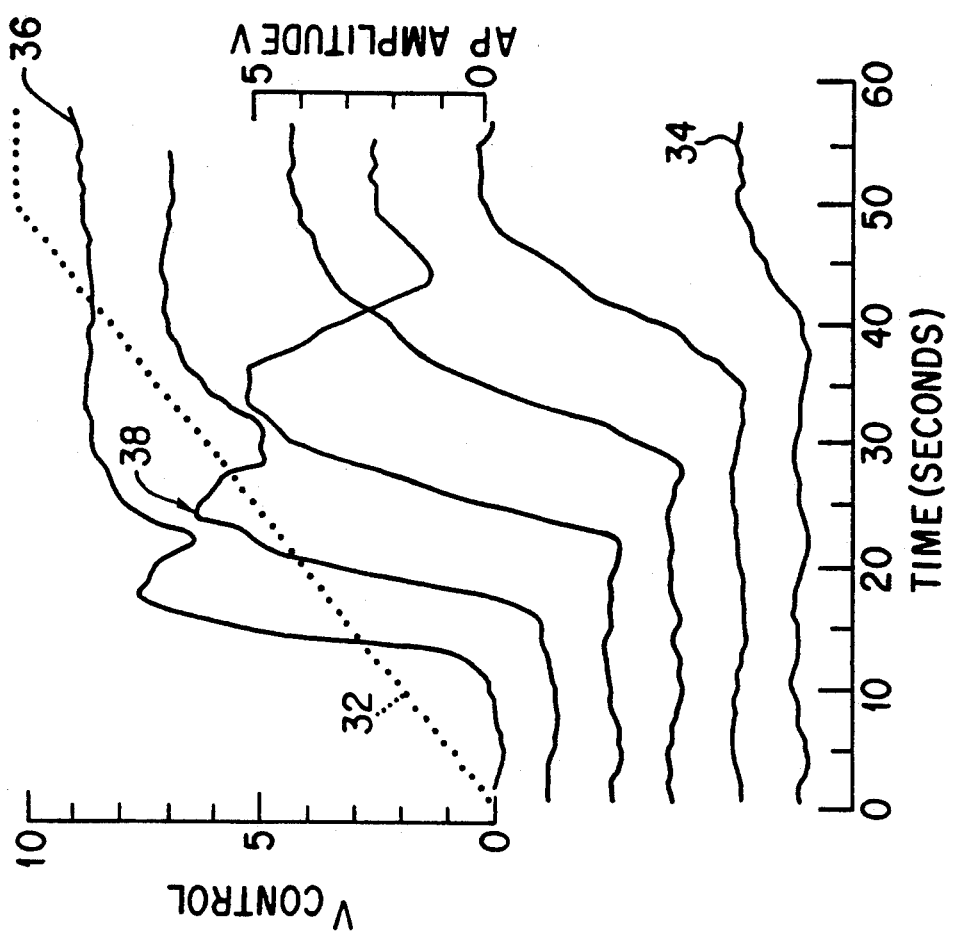

FIG. 3 illustrates the plotting of peak action potentials against stimulus magnitude at several fixed distances. $V_{control}$ 32 was set to increase linearly over the course of 50 seconds from 0 V, where stimuli pulses were 0.01 mA and 56 μs duration, to 10 V, where stimuli were 24.5 mA and 570 μs in duration. This progressive increase in stimulus magnitude was repeated at six different needle positions ranging from touching the nerve (distance=0) to 6.25 cm above the nerve in 0.125 cm increments. The growth of the peak action potential with time as the stimulus increased is plotted (in volts after 1000× amplification) at each distance, with curve 34 taken at the most distant needle position and curve 36 taken with the needle on the nerve. With the needle on the nerve (curve 36), action potentials reaching AP-LEV began to appear after 11 seconds as $V_{control}$ reached 2 V. At more distant locations, $V_{control}$ had to be higher for stimuli to be successful; that is, for the stimuli to elicit responses equal to or greater than the AP-LEV. Thus, the plots of peak amplitudes, 38, for example, do not rise above baseline until later in the "ramp" of $V_{control}$ when stimuli had increased above the threshold for activation of nerve fibers. The dips in the upper three curves appear in the record of peak action potentials (even as $V_{control}$ increases) as a reflection of the subtractive effects of slower conducting fibers within the nerve. FIG. 3A shows the nerve's response to a maximal stimulus with the needle on the nerve, while FIG. 3B shows the nerve's response to a maximal stimulus with the needle 0.762 cm from the nerve.

The D-LEV criterion level is the lowest amount of voltage which stimulates the nerve when the stimulating needle is within 500 μm of the target nerve. This is the value to which $V_{control}$ ultimately converges, signaling localization of the target nerve. For in vitro experiments, the setting for D-LEV was determined by moving the needle tip 0.5 mm away from the target nerve and recording the voltage for the stimulus pulses that were effective in producing action potentials equal to or greater than AP-LEV. A setting of 1.25 to 1.30 V (corresponding to stimuli of 0.8 mA and 160 µs) worked well for most of the in vitro experiments. In use, the nerve is "found" when the $V_{control}$ drops below the D-LEV. At this point, the stimulating needle is now within 0.5 mm of the target nerve and no further advancement of the needle should be made, which should avoid damage to the nerve.

Figure 4:
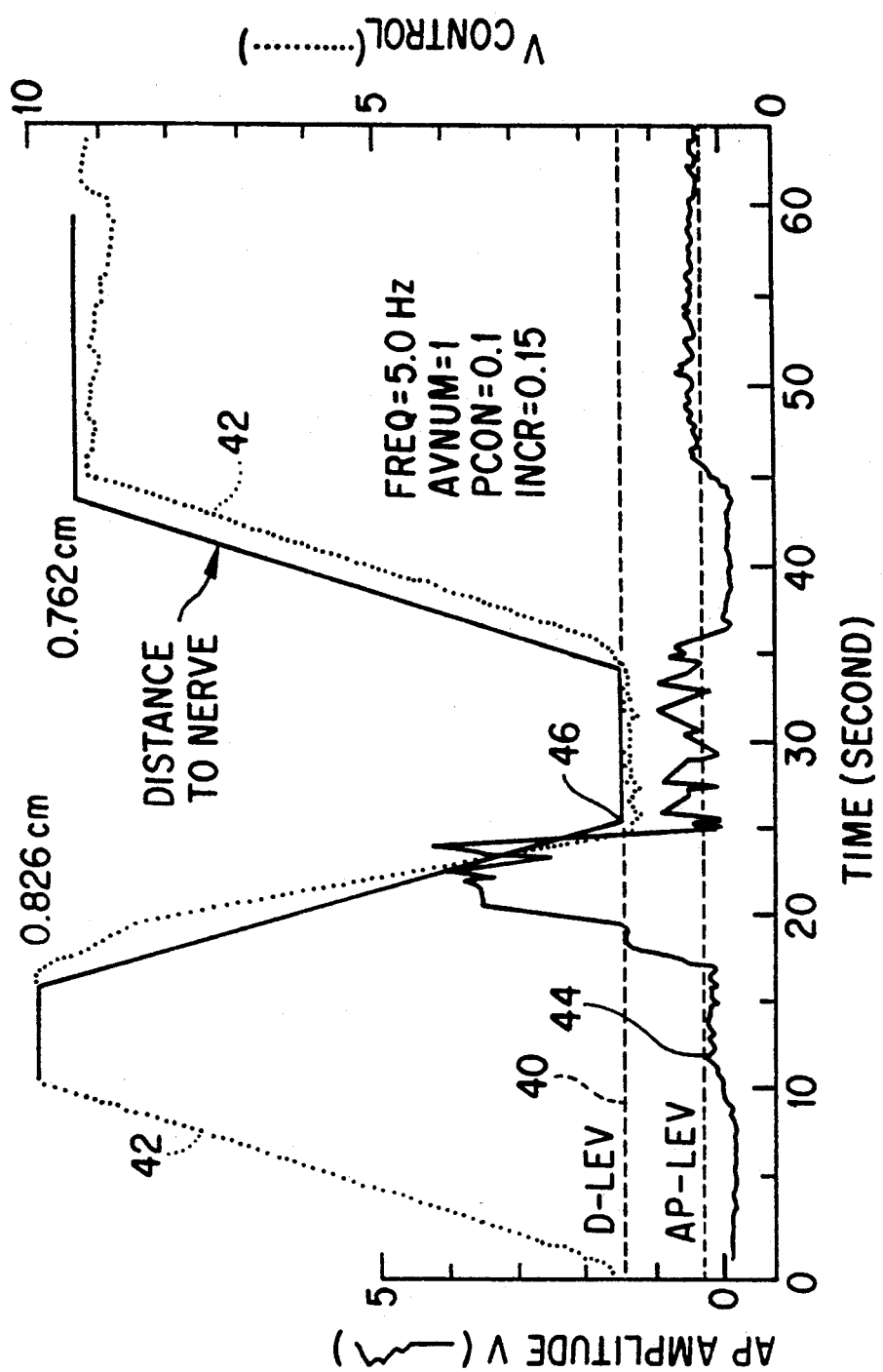
FIG. 4 is a graph showing the tracking of the stimulus delivery means and arrival of the needle at the nerve during an approach.

Turning to FIG. 4, the stimulating needle of the present invention was stationed 0.826 cm above the nerve. The record began with $V_{control}$ set low (at D-LEV, dashed line 40, the level corresponding to the stimulus strength required to produce a criterion action potential when the needle was within 0.5 mm of the nerve). At 0–10 seconds, stimuli were too weak to activate any nerve fibers with the needle at this distance. $V_{control}$, dotted line 42, rose incrementally resulting in a maximum stimulus (19.6 mA and 580 µs) after 11 seconds. This stimulus evoked an action potential 44 whose peak amplitude was just below AP-LEV. At 16 seconds the needle was moved steadily towards the nerve by constant rate rotation of the micrometer. As the peak of the evoked action potential rose above AP-LEV, $V_{control}$ was reduced. As the action potential increased, the descent of $V_{control}$ steepened. At approximately 26 seconds (point 46) the needle reached within 0.5 mm of the nerve and advance of the needle was halted as $V_{control}$ dropped below D-LEV. $V_{control}$ thus serves as the parameter that indicates distance of the needle from the nerve. With the needle near the nerve, the peak values of action potentials hover around AP-LEV and $V_{control}$ hovers at D-LEV. At 34 seconds into the test, the needle was withdrawn along the same path stopping 0.762 cm above the nerve, where a criterion action potential was sustained as $V_{control}$ hovered between 8.7 and 9.3 V (corresponding to stimuli of 18.2 mA and 510 µs duration).

The third criterion parameter, VMAX, establishes a voltage ceiling limiting $V_{control}$ (and thus the magnitude of the stimulus produced by the stimulator circuit) to avoid undesired events such as substantial contraction of muscles or activation of high threshold unmyelinated fibers, or other small diameter myelinated fibers which will cause a painful sensation if stimulated. A high $V_{control}$ may be useful in some procedures to ensure that a signal is elicited even when the needle is far away from the target nerve. However, for procedures where it is easy to put the needle within a centimeter of the target nerve on the basis of anatomical cues alone, such high magnitude stimulation is not necessary. For the in vitro experiments, VMAX was set at 10 V, corresponding to stimulus pulses of 20 mA and 500 µs in duration, limiting the effective stimulation distance to approximately 1 cm.

TRACKING CONTROL PARAMETERS

There are four interdependent parameters which govern the rate, accuracy and stability of tracking the needle position relative to the nerve. These parameters include a proportionality constant parameter (PCON), a linear increment constant parameter (INCR), an update frequency parameter (FREQ), and an averaging parameter (AVNUM).

During the in vitro experiments, methods were formulated for tracking the location of the needle vis-a-vis the target nerve. The first tracking strategy was to adjust the $V_{control}$ by constant increments if the evoked action potential peak was below AP-LEV or by constant decrements if the evoked action potential was above AP-LEV. Tracking rates were thus constant at a level determined by the frequency of testing and the size of the increments and the decrements. However, it was determined with variable insertion rates that constant rate tracking is not accurate. Variable insertion rates resulted in high magnitude stimuli near the nerve, producing large action potentials which would cause strong and possibly painful sensations to a patient. This problem was corrected by using a proportional method to decrease the stimulus. The reduction was determined by a factor, PCON, times the difference between the peak amplitude of the action potential and the AP-LEV. By proportionally decreasing the stimuli, the stimuli decrease quickly whenever the evoked action potential is well above the selected AP-LEV.

For in vitro experiments, the larger the PCON value was set, the more $V_{control}$ changed from trial to trial to compensate for stimuli generating large action potentials. However, if PCON was too high, the changes in $V_{control}$ elicited widely varying action potentials, making it difficult for the user to guide the needle to the nerve. In vitro experiments revealed that a PCON setting of 0.20 to 0.40 allowed quick downward adjustment of stimulus current levels without sacrificing close tracking control. With reference to FIG. 5A, notice that with a PCON of 0.3, $V_{control}$ 42 was quickly reduced as peak action potential value 44 exceeded AP-LEV 48 (evidencing approach to the nerve). However, if the PCON was set too low (e.g. PCON=0.020), tracking was delayed and slow. As shown in FIG. 5B, $V_{control}$ did not drop to D-LEV 40 until almost five seconds after the needle had already found the nerve, and at that time (36 seconds into the test) the needle was past the nerve. Thus, with a low PCON value, nerve locator 10 fails to accurately track and indicate localization of the target nerve.

During withdrawal of the needle, linear increments were found to be better than proportional changes in $V_{control}$. When the needle is withdrawn or realigned, the key information to be had from $V_{control}$ is that the distance is increasing, and it is not necessary to have the magnitude of the stimulus rise dramatically in an attempt to track distance during withdrawal. In vitro experiments showed that it was more effective for the user to alter the needle position so that successful stimulation at the reduced level occurred. If this repositioning required a considerable amount of time, $V_{control}$ increased at a rate of linearly incremental (INCR) volts per trial until the stimulus again produced an action potential above the AP-LEV. INCR should therefore be large enough to track increases in distance, but small enough to avoid oscillations in $V_{control}$ when the needle is at rest near the nerve. At 5.0 Hz, in vitro experiments revealed that an INCR setting of 0.12 V was appropriate.

Update frequency (FREQ), the third tracking parameter, ranges from 0.5 to 25 Hz and specifies the rate at which the system finds the peak of the (averaged) action potentials, adjusts the $V_{control}$ and varies the audible tone and/or updates the graph displayed on the computer monitor or spoken voice. It is of obvious importance to find the rate of signaling changes in $V_{control}$ that is most effective for guiding movement of the needle. At high frequencies (which would result in a high rate of nerve discharge), intrinsic changes in the excitability of nerve axons will alter the peak of the action potentials independently of the position of the needle. After experimenting with several frequencies, it was found that frequencies below 5.0 Hz are too slow, making updates seem discontinuous to the user. However, frequencies above 10.0 Hz usually result in overstimulation of the target nerve. In vitro frog experiments revealed that the preferred frequency was between 5.0 Hz and 10.0 Hz. It was also found that frequencies could be adjusted for nerves of different species. For example, mammalian nerves could accept a higher frequency without risk of overstimulation.

Finally, the AVNUM parameter takes into account the fact that transcutaneously recorded action potentials are sometimes difficult to discern from noise in single trials. In view of this noise, nerve locator 10 incorporates optional averaging of up to ten signals per update before evaluating the peak height and adjusting the $V_{control}$. The number of signals to be averaged per trial are thus specified by the AVNUM parameter.

Several in vitro and in vivo experiments were performed to optimize these various parameters. The constraints on optimization were investigated for 1) the tracking speed of both linear advancement and oscillatory motions of the needle, 2) the stability of the system with the needle stationary, and 3) tracking needle movement with a limit of 1.0 Hz on the stimulation rate.

Generally, the tracking capability increased with the update frequency (FREQ) because adjustments to the stimulus were made more often. Accuracy also increased with FREQ since a given tracking rate could be preserved with smaller changes in $V_{control}$ per update. 10 Hz was found to be a good update frequency, tracking needle motion accurately as fast as 0.2 cm/s with a PCON setting of 0.125 and an INCR setting of 0.125.

Figure 6A:
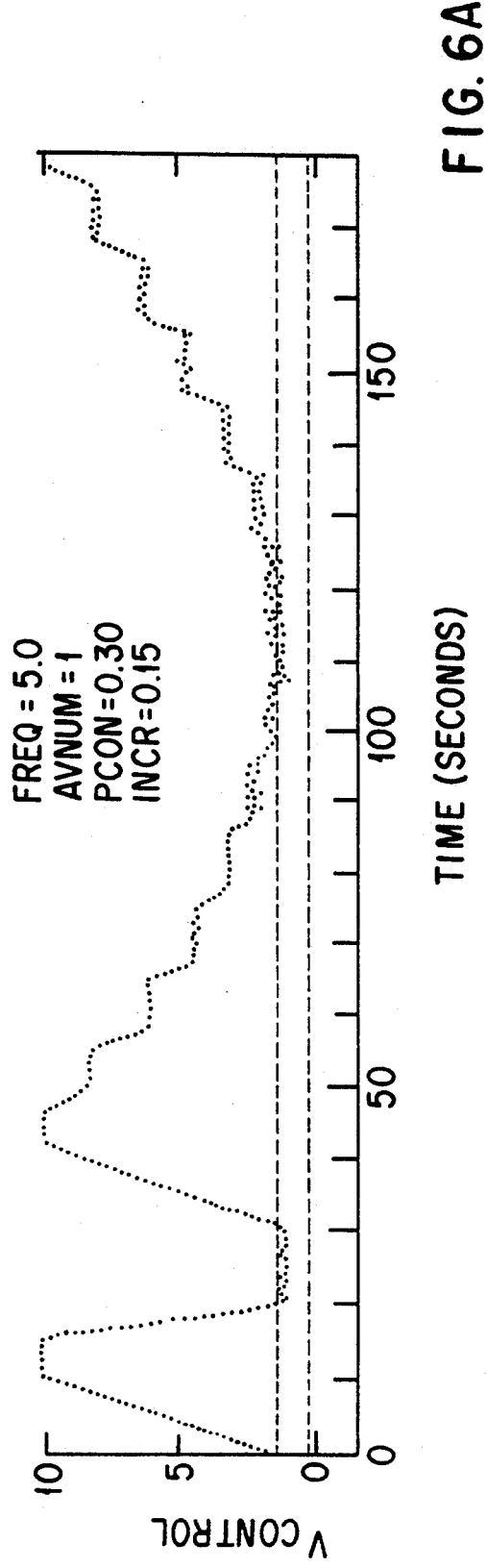
FIG. 6 is a series of graphs showing stepwise changes in the position of the stimulus delivery means of the nerve locating embodiment.
Figure 6B:
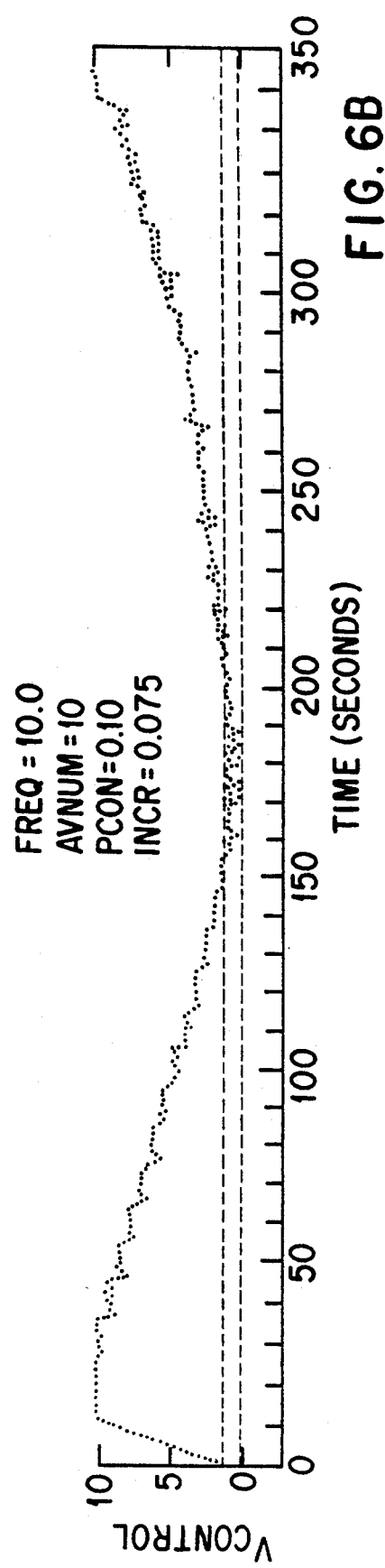

A sign of instability of the device is the presence of large fluctuations in $V_{control}$ while the needle is stationary. The significant causes were found to be overstimulation (high FREQ and AVNUM) and/or large increments and decrements (INCR and PCON). With reference to FIG. 6, stability was tested using a stepwise approach to the nerve in which the position of the needle was temporarily held and then advanced quickly by a step. Such stepwise displacements were followed well with an update frequency of 5 Hz and PCON and INCR settings of 0.30 and 0.15, respectively (FIG. 6A). However, stimulation at high frequencies (100 Hz, FIG. 6B) resulted in oscillations of $V_{control}$ following each step. Localizing the nerve was not impeded at such high update frequencies, but the peak action potentials under these conditions oscillated from 0 to near maximum, phase-locked with $V_{control}$ even if PCON and INCR were reduced (PCON=0.10, INCR=0.075). These step experiments show the significance of discharge frequency and activity dependent threshold changes, demonstrating the tradeoffs to be expected in particular applications. Since fibers differ widely in degree of activity dependence, it may useful to "tune" the device to match the characteristics of a nerve being localized, which tuning is available in the locator 10 by software adjustment of the tracking parameters.

Figure 7:
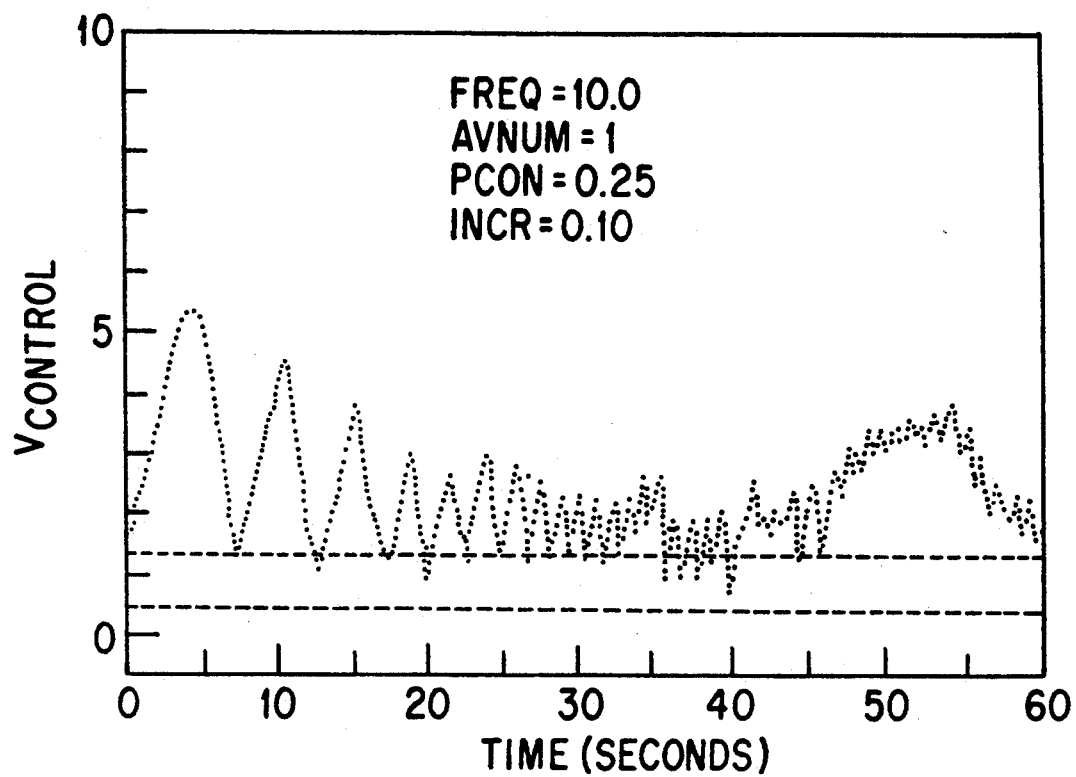
FIG. 7 is a graph showing the tracking of the distances to the nerve during oscillatory motion of the nerve locator embodiment.

In vitro and in vivo experiments also involved short distance, oscillatory needle movements in order to determine the maximum frequency of cyclic motion that could be tracked. With reference to FIG. 7, the needle was moved back and forth (0.5 cm) at increasing frequencies until the $V_{control}$ was no longer able to respond to each cycle. For these experiments the tracking algorithm implemented proportional adjustments as the needle approached the nerve and constant increments as it moved away from it. Needle motion was easily tracked for frequencies around 0.2 Hz and it remained phase-locked for cyclic motions as high as 1.0 Hz (see FIG. 7, results within 0–38 seconds). At higher frequencies, around 2.0 Hz (results at 45 seconds), the device missed cycles. These trials were performed without averaging and with a PCON of 0.20 to 0.30.

Figure 8:
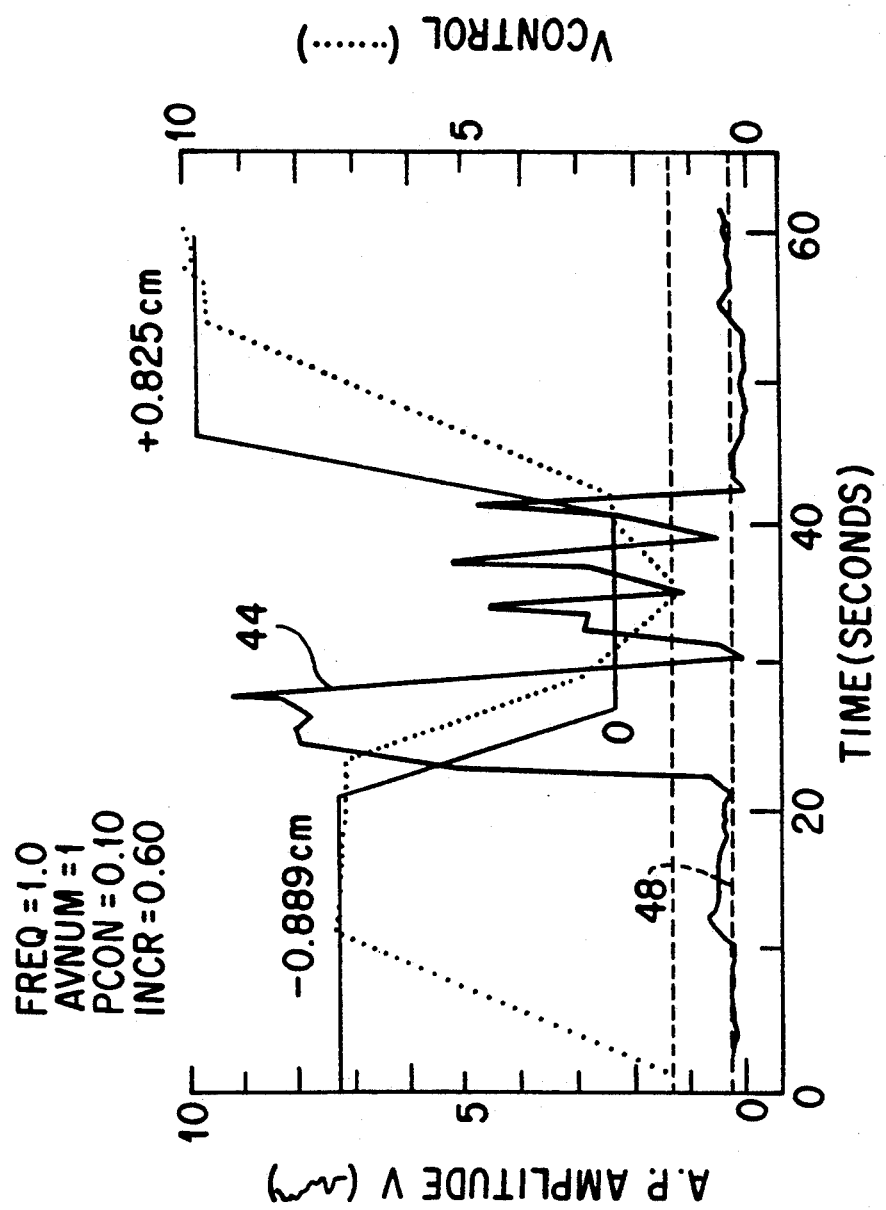
FIG. 8 shows the performance of the nerve locator embodiment operated at a frequency of 1 Hz.

Lastly, because most commercially available nerve stimulators stimulate the nerve at 1 Hz, the tuning of the device for optimum performance at 1 Hz was also examined. While tuning at 1 Hz resulted in a tracking rate of 0.7 cm/s, it allowed action potential peaks 44 to get many times larger than the AP-LEV 48 (see FIG. 8). Large action potentials were unavoidable at 1 Hz if the system was to track needle insertion, even using proportional adjustment of $V_{control}$. Increasing PCON (up to 0.750) increased tracking speed, but steady-state instability of $V_{control}$ with a stationary needle exceeded 30% of its range, which had the effect of delaying the device's reaction by five seconds or more after withdrawal of the needle began. With a PCON setting of 0.10 (as in FIG. 8), the increase of $V_{control}$ began right after the first test following the start of withdrawal (at 40 seconds). At 1 Hz, INCR needed to be large (0.60) to track withdrawal rates of 0.1 cm/s, reducing stability. With smaller INCR setting, which tended to work well at higher update frequencies, the device took nearly a minute to adjust the $V_{control}$ enough to indicate 0.7 cm of needle movement that actually occurred over seven seconds. Thus, in terms of finding the nerve quickly and maintaining sensible and influential feedback, a frequency of 1 Hz was found to be too low.

The results of in vitro and in vivo experiments show that for successful stimulation and tracking, the parameters of stimulus modulating means 16 should be set within the following ranges:

| | |
|---|---|
| AP-LEV = | 5–8% of maximum amplitude of the fastest conducting elevation of the action potential |
| D-LEV = | 1.25 to 1.30 V |
| VMAX = | 10 V |
| PCON = | 0.20 to 0.40 V |
| INCR = | 0.12 to 0.15 V |
| FREQ = | 5 to 10 Hz |
| AVNUM = | 1 to 5 |

Having discussed the hardware, software and parameter definitions of the software program, the method of use of nerve locator 10 for anesthesia purposes will now be described. With the patient prepared for the procedure, electrodes 15 are affixed to the patient's body in an appropriate location relative to the target nerve. The sequence of stimulus control means 16 includes an initial set-up stage where the user sets each of the aforedescribed parameters to "tune" the nerve locator's performance to the user's preferences and the nerve type. The set-up stage is optional, and if the set-up stage is omitted, the parameter settings default to the settings in place at the end of the last use of the device, or they can all be reset to the values recommended by the manufacturer simply by invoking a "reset all" feature.

If desired, the user sets the following paremeters: 1) AP-LEV; 2) INCR; 3) PCON; 4) FREQ; 5) AVNUM; 6) D-LEV; 7) VMAX; 8) the sweeplength which establishes the interval after each stimulus that the recorded channel will be digitized; and 9) the file specifications for the record to be taken during stimulation.

Following set-up of the nerve locator sequence, a file is opened for the data, and the needle to nerve distance indicator 18 shows the initial levels and settings. An update loop is initiated thereafter.

Stimulating probe 22 is inserted or placed into the body tissue proximate the target nerve N. The acquisition program is called forth and stimulus control means 16 sends a biphasic voltage pulse to stimulator circuit 20. Stimulator circuit 20 converts the pulse into a biphasic square current pulse and sends this current to stimulating probe 22. Responses to the initial pulse are recorded by electrodes 15 of response-detecting means 14. The recorded action potentials are digitized for the sweeplength, which has been previously set long enough to accommodate the delay between a stimulus and a response recorded from activation from activation of the target nerve N. The digitized values are added to an array that stores analog-digital samples. These first two steps are repeated as dictated by the AVNUM parameter set by the user in the initial set-up stage. The array is then scanned and the peak action potential value determined. The value corresponding to the stimulus strength ($V_{control}$, which reflects distance of probe 22 to nerve N) is plotted on the display screen of the computer monitor together with the peak action potential value. This peak value is compared to the AP-LEV parameter as set in the initial set-up stage. If the peak action potential is below AP-LEV, $V_{control}$ is augmented, increasing the output of the stimulator circuit 20 by an amount dictated by the INCR parameter. On the other hand, if the peak action potential is above AP-LEV, $V_{control}$ is reduced as directed by the PCON parameter, thus resulting in a reduced stimulus from circuit 20. This new $V_{control}$ value and the peak action potential value are plotted on the monitor of the computer to indicate the distance of the needle from the target nerve N at that point in time. If the audio needle to nerve distance indicator 18' is activated, the tone will become higher in pitch if the $V_{control}$ amplitude and the stimulus pulse from circuit 20 is lower than for the previous pulse, or the tone will become lower in pitch if the $V_{control}$ is of a higher voltage. Probe 22 is advanced within the tissue until the $V_{control}$ amplitude descends to the value of the D-LEV as set in the initial set-up stage. As $V_{control}$ drops below D-LEV, the audible tone jumps to a very high pitch indicating that target nerve N has been "found" (that is, probe 22 is within 0.5 mm of the target nerve). Alternatively, a speech synthesizer module will announce that the nerve has been located.

At this time, a portion of the anesthetic (a test injection) is administered to the target nerve N through needle (probe) 22. If the response of the nerve or end organ to a D-LEV value pulse ceases, then the test injection has been administered in the optimum area either displacing the nerve from the needle tip or pharmacologically blocking the response. Normally, the remaining dose of anesthetic is then administered to the patient. Thus, for regional anesthesia purposes the nerve locator of the present invention is able to track probe (needle) movement successfully; maintain feedback stability in a steady-state needle position; record changes in the direction of needle movement; and report when the probe is about to come into contact with the target nerve.

NERVE GUARDING AND MONITORING

While the nerve locator of the present invention effectively locates peripheral nerves for regional anesthesia purposes, a modified version can also locate and/or monitor the integrity of nerves for surgical purposes. As discussed earlier, a nerve locator may be used during surgical procedures (e.g. during tumor excision surgery) to guard against inadvertent cutting. For this purpose, called "nerve guarding", a nerve locator assists in testing and monitoring certain nerves which are critical for specific voluntary and involuntary motor functions. For example, during prostatectomies (removal of the prostate gland), the operating surgeon strives to avoid cutting nerves in the pelvic region which are responsible for producing an erection. Thus, a nerve locator is valuable for not only locating nerves but for testing and monitoring the integrity of nerves that are responsible for specific motor functions.

An alternate embodiment of the nerve locator of the present invention has been adapted for this purpose. Its structure and method of use will now be described. For illustrative purposes only, this alternate embodiment of the present invention will be discussed as used for a prostatectomy. However, it should be realized that this embodiment may be used for any surgical procedure where guarding of the nerve is desired (e.g., facial surgery).

Figure 9:
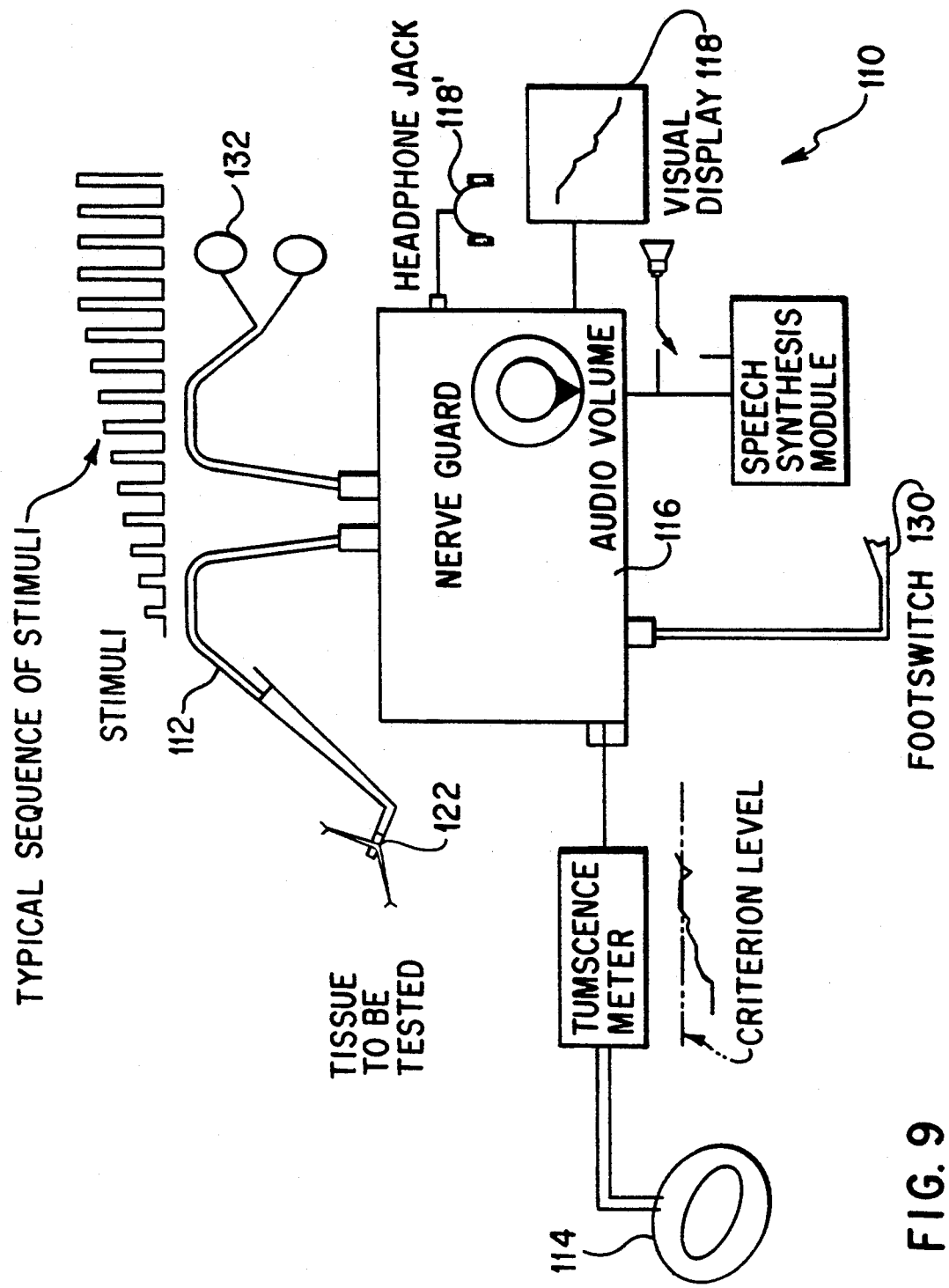
FIG. 9 is a schematic drawing of the component parts of an alternate embodiment of the present invention for monitoring nerve integrity and preventing inadvertent cutting (guarding) of nerves during surgery.

With reference to FIG. 9, the alternate embodiment of the nerve locator of the present invention for nerve guarding is shown generally at 110. Similar to nerve locator 10, the nerve guard 110 generally comprises a stimulus delivery means 112, a response-detecting means 114, and a stimulus generating and control means 116.

Stimulus generating and control means 116 includes a computer having a data acquisition board similar to that previously described which generates a symmetric biphasic square pulse current. The voltage-controlled current generator of stimulus generating and control means 116 controls the magnitude of the pulse delivered to the tissue to regulate the degree of the physiological response as assessed from the response-detecting means 114.

In the example discussed, the stimulus generated by stimulus generating and control means 116 is delivered to the pelvic tissue by stimulus delivery means 112. Stimulus delivery means 112 includes a probe 122 for delivering the stimulus to the tissue to be sectioned. Probe 122 is insulated and is otherwise similar to conventional probes used by surgeons to elevate tissue prior to section. Probe 122 may also take the form of insulated surgical scissors or clamps, if desired.

Figure 10:
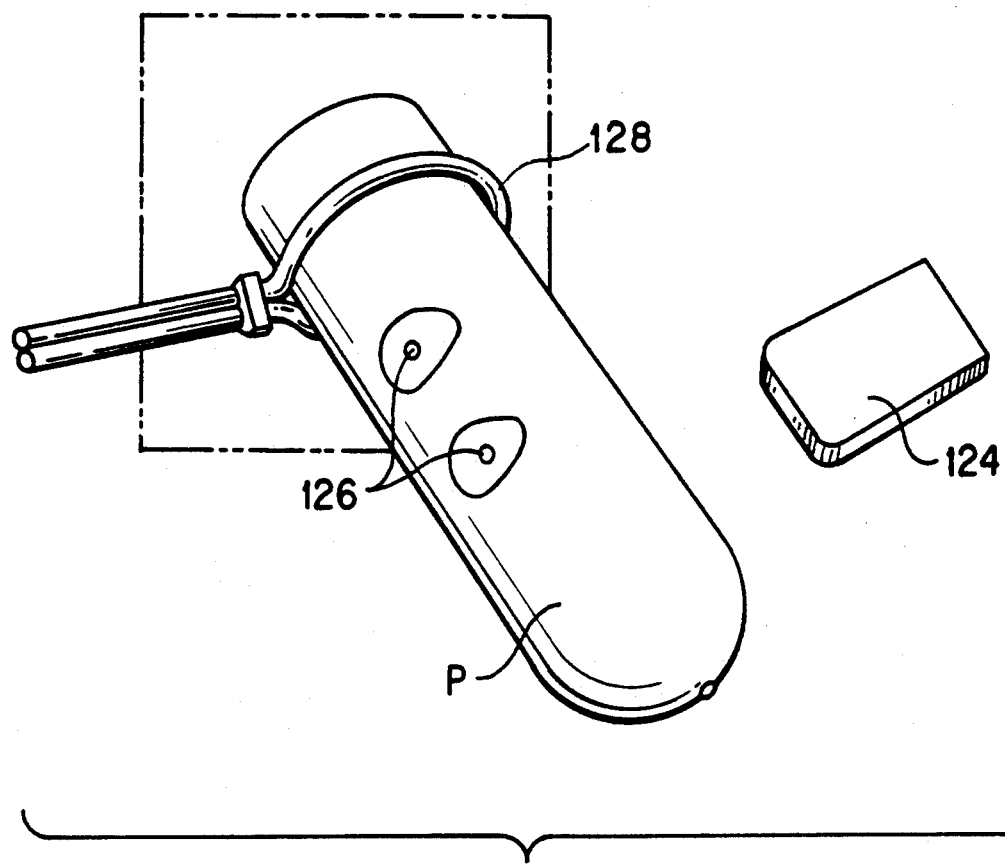
FIG. 10 illustrates various embodiments of the response-detecting means of the nerve guarding embodiment shown in FIG. 9.

Any response of nerve(s) that may be within the tissue will result in tumescence (increase in circumference, an increase in velocity of blood in penile arteries or reduction of the rhythmic contraction of cavernosal muscle) of the penis which is detected and recorded by response-detecting means 114. As shown in FIG. 10, response-detecting means 114 may be (1) a Doppler flow head 124 positioned on penis P so that it images the dorsal artery, (2) EMG electrodes 126 which are attached to the penis, or (3) mercury-filled distensible tubing 128 which is disposed about the penis such that tumescence changes the resistance of the tube. Additionally or alternatively, an accelerometer transducing muscle movement, or an observer can detect the response and signal the stimulus control means via a switch to automatically increase or decrease the stimulus. Depending upon the detector used, the response-detecting means must be capable of transducing a neurally induced change in the degree of tumescence. If EMG electrodes 126 are used as response-detecting means 114, an amplifier must be used to boost the detected signals to levels appropriate for analog-digital (A/D) conversion. The response detected by response-detecting means 114 is converted by an A/D converter and sent back to stimulus generating and control means 116. The response from response-detecting means 114 is received by the data acquisition board of the computer where it is evaluated for determining the strength of the next pulse generated by stimulus generating and control means 116 and stored. The data acquisition board and computer of stimulus control means 116 is run by hardware and software which is specifically written to determine whether the tissue on or near the probe contains nerves critical to the function at risk. The software of nerve locator 110 will be discussed in greater detail below.

In the preferred embodiment, stimulus control means 116 generates a $V_{control}$ signal that indicates proximity of the probe to the nerve to be guarded. The program generating $V_{control}$ also signals via an audible tone, a speech synthesizer module or visual display an indication of needle to nerve distance. For example, as tumescence of the patient's penis increases, the decreasing current delivered by the probe may be shown graphically on the computer monitor or via pitch of an audible tone or synthesized voice which is delivered to the surgeon through a headset (118').

Just as nerve locator 10 was governed by several parameters to control the stimulating pulse delivered to the nerve, the pulses delivered by the nerve guard 110 are also controlled by various parameters, according to four modes or "protocols" later described.

The first parameter is similar to the AP-LEV parameter of nerve locator 10 and is called the detection criterion level parameter (DETECT). This parameter is the criterion level for detection of successful activation of the nervous supply that is to be protected from inadvertent cutting. For cavernosal nerves this parameter would stipulate a minimal voltage of approximately 1 V from the output of the tumescence sensor 114.

The second parameter, INCR, is the increment for increasing the $V_{control}$ which in turn increases both the strength of the stimulus pulses and in this embodiment also their frequency when the output of the tumescence sensor is below the criterion level. An INCR setting of approximately 0.3 V is preferably used for cavernosal nerves.

$STIM_f$, the third parameter, is the range of stimulus pulse frequencies to be delivered. $STIM_f$ is changed by $V_{control}$, increasing with $V_{control}$ as described below.

PCON, the fourth parameter, is the proportionality constant for decreasing the $V_{control}$ and thus decreasing both the strength of the stimulus and the frequency of stimulus pulses when the output of the tumescence sensor is above the criterion level. For cavernosal nerves, a preferable PCON setting is approximately 0.25 V.

The fifth parameter, VMAX, is the maximum $V_{control}$, setting the maximum stimulus pulse duration, amplitude as well as the pulse frequency to be delivered to the tissue. VMAX corresponds to the farthest distance from the probe that the user will still consider too close to the nerve to be spared. A VMAX setting of approximately 5 V is preferred for cavernosal nerve fibers, but will vary depending on the probe selected.

The nerve guard 110 also includes the $STIM_f$ parameter which sets the range of frequency of stimulation of cavernosal nerves, but does not affect the update frequency FREQ, which is set according to the dynamics of the neural system being tested. For cavernosal nerve fibers, a $STIM_f$ of 5-20 Hz and a FREQ value of approximately 0.5-3 Hz are appropriate, reflecting the delayed response (tumescence) following an increase in the magnitude and/or rate of stimulation of cavernosal nerve fibers.

Furthermore, the software program of nerve locator 110 may be manually overridden to prevent further stimulation if the stimulus pulse produces an undesired result such as muscle movement, micturition, etc.

The software program of nerve guard 110 is different from the nerve locator 10 in that it allows the user to choose from five separate pulse protocols. Four protocols are concerned with stimulation through the probe. The "query" protocol starts the stimulus magnitude at a user selected low value and increases at a user-specified rate until it reaches a specified limit (VMAX) or a criterion response equal to the DETECT parameter is detected. It is used to test a particular tissue held on the probe for the presence of functionally important nerve fibers.

The "last" protocol starts the stimulus magnitude at the last used magnitude and hunts up or down from that magnitude depending on the present output from the response-detecting means. The hunting phase continues for a duration set by the user. If the last protocol is initiated, the user will have to set a duration parameter not previously discussed to govern the duration of the hunting phase. This protocol is used to search the direction of probe movement that brings the probe nearer to the nerve.

The "fixed" protocol fixes the stimulus magnitude and rate to a particular level that is then controlled by the user through manual controls rather than automatically.

The fourth protocol, "hunt", starts the stimulus magnitude and $STIM_f$ either at the selected low value or at the last used magnitude and rate, and the system then adjusts both magnitude and rate so as to maintain a criterion response. Hunting continues until the user deactivates the stimulus pulse using a switch. This protocol is used to locate nerves using the probe in the same manner as the nerve locator used the needle. The user may switch among the different protocols at any time throughout the nerve location and identification procedure.

The fifth protocol, the "monitor" protocol, is analogous to the hunt protocol but uses electrodes 132 that are located outside the surgical field to stimulate the nerve. The nerve guard will increase the $STIM_f$ and stimulus magnitude by raising $V_{control}$ as needed to maintain the degree of tumescence at DETECT. In this mode, the deleterious effects of cutting nerves will be revealed in a progressive increase of $V_{control}$. The monitor protocol can operate in parallel with the probe protocols.

Having discussed the hardware, software and parameter definitions of the software program, the method of use of the nerve guard 110 for surgical purposes will now be described with regard to a prostatectomy.

With the patient prepared for surgery, response-detecting means 114 is affixed to the penis of the patient.

The sequence of stimulus generating and control means 116 includes an initial set-up stage where the user sets each of the parameters to tune the performance of the nerve guard 110 to the user's preferences. This set-up stage is optional, and if the set-up stage is omitted, the parameter settings default to the settings in place at the end of the last use of the device or to the settings recommended by the manufacturer (reset-all). After setting the aforementioned parameters and with the tissue to be sectioned elevated on stimulating probe 122, the user activates the nerve guard 110. In a preferred embodiment, nerve guard 110 is activated by a foot switch 130 shown in FIG. 9. A file is opened for the data, and the visual display shows the initial stimulus levels and parameter settings. An update loop then begins. The data acquisition program is called forth and the appropriate protocol of pulses and pulse amplitudes is generated in the form of biphasic square pulse currents and sent to stimulus delivery means 112. The remainder of this discussion is based on the query protocol.

The stimulating pulse from stimulus generating and control means 116 is delivered to the elevated tissue through stimulating probe 122. If response-detecting means 114 detects no tumescence at the level of the DETECT value set during the set-up stage, stimulus generating and control means 116 generates a higher $V_{control}$ level as dictated by the INCR parameter. Using the query protocol, no response will be detected by response-detecting means 114 as the $V_{control}$ is too low to generate stimuli of sufficient amplitude and rate to produce tumescence in the patient's penis. The stimulus pulse generated by stimulus generating and control means 116 will thus continue to increase as $V_{control}$ rises until response-detecting means 114 gives an output value equal or greater than the value of DETECT. When response-detecting means 114 gives an output value equal to or greater than DETECT, stimulus generating and control means 116 will vary successive stimuli so as to maintain the level of response. If response-detecting means 114 continues to detect tumescence equal to the value of DETECT with the $V_{control}$ less than VMAX, then the tissue elevated on the probe most likely contains cavernosal nerve fibers. Thus, the surgeon will not section the tissue on the probe unless overriding health conditions require it. Throughout the location and guarding procedure, tumescence indicators 118 and 118' indicate to the user the $V_{control}$ required to maintain tumescence of the patient's penis. For example, as the train of current pulses generated by stimulus generating and control means 116 increases in intensity and rate, the audible tone of tumescence indicator means 118' decreases in pitch. As the pitch levels off to a maintained continuous tone, the user is thereby informed that the tissue on the probe contains sufficient nerve fibers to produce a criterion level of tumescence and which are partly responsible for producing an erection. Thus, while looking only at the surgical field, the user will know the intensity of the stimulus being applied and if the tissue on the probe contains cavernosal nerve fibers. The visual display (118) also displays the trend of stimulus strengths throughout the test procedure. The increasing $V_{control}$ results in stimulus pulses of increasing magnitude and increasing frequency. As $V_{control}$ levels off the user is informed as to the relative degree that the tissue contains nerve fibers essential for erection.

When nerve guard 110 is in the hunt or last protocol modes, the aforementioned events are repeated and the output values of response-detecting means 114 are compared to the value of DETECT. Appropriate adjustments are then made to the stimulus pulse magnitude and rate by stimulus generating and control means 116 to test for the proximity of the probe to the nerve. Thus, using the "hunt" or "last" protocols of nerve guard 110, the proximity of the probe to the nerve as well as the function of the nerve may be determined in a safe and accurate manner.

For surgical purposes, the nerve guard of the present invention is able to successfully confirm that tissue contains nerves that are critical to important functions of the body effectively and accurately, thereby permitting the surgeon to spare nerves which are essential for specific body functions. Moreover, using various stimulus protocols, the user may also determine the location of nerves within body tissue in relation to the stimulating probe.

MONITORING

Additionally, by using stimulating electrodes placed near the source of the nerve supply in question such that impulses so generated will traverse from one side of the operated area to the other, it is possible to use the nerve guard to monitor the integrity of the nerve pathway. The electrodes are initially set so that a criterion level of response (such as tumescence) is produced. Then as the surgeon may interrupt portions of the nerve supply, the $V_{control}$ will rise as the rate and intensity of stimuli to the remaining nerves having the same function is increased to maintain the response. By gauging the degree of change in the tone signal proportional to $V_{control}$ or by looking at the video plot, the surgeon can assess the degree of damage done to the cavernosal nerves.

It is to be understood that the foregoing is considered as illustrative only of the principles of the invention. Therefore, within the scope of the appended claims, the invention may be practiced otherwise than as specifically described herein.

We claim:

1. A method for locating a nerve comprising the steps of:
   (a) delivering a stimulus to a nerve using a stimulus delivery means;
   (b) detecting the response of said nerve to said stimulus using a response detecting means;
   (c) determining the distance of said nerve from said stimulus delivery means by comparing the response of said nerve to said stimulus against a predetermined criterion;
   (d) modifying the next stimulus to be delivered to said nerve, wherein said next stimulus is automatically modified by a control means which continually modifies the next stimulus delivered to said nerve based on the response of the nerve to the previously delivered stimulus so as to hold the level of the nerve's response substantially constant at a predetermined value;
   (e) conveying to the user the distance between said stimulus delivery means and said nerve;
   (f) repositioning said stimulus delivery means in relation to said nerve; and
   (g) delivering said next stimulus to said nerve using said stimulus delivery means.

2. The method of claim 1, wherein steps b-g are repeated.

3. The method of claim 1, wherein steps b-g are repeated until the output of said response detecting means reaches either a predetermined upper or lower limit.

4. The method of claim 1, wherein steps b-g are repeated until said next stimulus is modified to a maximum value.

5. The method of claim 1, wherein steps b-g are repeated until said next stimulus is modified to a minimum value.

6. The method of claim 5, further comprising the step of holding said next stimulus substantially at said minimum value, wherein said minimum value has previously been shown to correspond to an interpretable state such as the stimulus delivery means being within a certain distance of the nerve.

7. The method of claim 5, wherein said stimulus delivery means is a hypodermic needle.

8. The method of claim 7, further comprising the step of injecting a drug through said needle.

9. The method of claim 1, wherein said control means modifies the intensity of said stimulus.

10. The method of claim 1, wherein the distance between said stimulus delivery means and the nerve is conveyed by an audible tone.

11. The method of claim 1, wherein said response detecting means comprises at least one pair of electrodes.

12. The method of claim 1, wherein said nerve is a mixed peripheral nerve.

13. The method of claim 12, wherein said mixed peripheral nerve is the sciatic nerve.

14. The method of claim 1, wherein said stimulus delivery means is a hypodermic needle.

15. The method of claim 1, wherein said control means modifies the duration of said stimulus.

16. The method of claim 1, wherein said control means modifies the frequency of said stimulus.

17. The method of claim 1, wherein said nerve is a pelvic nerve.

18. The method of claim 17, wherein said response detecting means is a tumescence monitor.

19. The method of claim 18, wherein said stimulus delivery means is a surgical instrument.

* * * * *

UNITED STATES PATENT AND TRADEMARK OFFICE
CERTIFICATE OF CORRECTION

PATENT NO. : 5,284,153
APPLICATION NO. : 07/868387
DATED : February 8, 1994
INVENTOR(S) : Raymond et al.

It is certified that error appears in the above-identified patent and that said Letters Patent is hereby corrected as shown below:

Column 1, please delete the paragraph under "STATEMENT AS TO RIGHTS TO INVENTIONS MADE UNDER FEDERALLY-SPONSORED RESEARCH AND DEVELOPMENT" and replace it with the following:
This invention was made with Government support under Grant No. GM035647 awarded by the National Institutes of Health. The Government has certain rights in this invention.

Signed and Sealed this

Seventeenth Day of November, 2009

David J. Kappos
*Director of the United States Patent and Trademark Office*